United States Patent
Chavan et al.

(10) Patent No.: US 9,527,800 B2
(45) Date of Patent: Dec. 27, 2016

(54) PROCESS FOR TOTAL SYNTHESIS OF VENLAFAXINE

(71) Applicant: Council of Scientific and Industrial Research, New Delhi (IN)

(72) Inventors: Subhash Prataprao Chavan, Pune (IN); Kailash Pralhad Pawar, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/033,506

(22) PCT Filed: Oct. 29, 2014

(86) PCT No.: PCT/IN2014/000687
§ 371 (c)(1),
(2) Date: Apr. 29, 2016

(87) PCT Pub. No.: WO2015/063791
PCT Pub. Date: May 7, 2015

(65) Prior Publication Data
US 2016/0272573 A1    Sep. 22, 2016

(51) Int. Cl.
C07C 213/08    (2006.01)
C07C 67/42     (2006.01)
C07C 29/147    (2006.01)

(52) U.S. Cl.
CPC ........... C07C 213/08 (2013.01); C07C 29/147 (2013.01); C07C 67/42 (2013.01); C07C 2101/14 (2013.01)

(58) Field of Classification Search
CPC .................................................. C07C 213/08
See application file for complete search history.

(56) References Cited

U.S. PATENT DOCUMENTS 6,756,502 B2    6/2004  Rathod et al.
2007/0135449 A1  6/2007  Mahaney et al.

FOREIGN PATENT DOCUMENTS

GB   2173787           10/1986
WO   WO-2010/046808    4/2010
WO   WO-2015/063791    5/2015

OTHER PUBLICATIONS

Hoshino et al. Bull. Chem. Soc. Jpn. 73(7), 2000, 1653-1658.*
"International Application No. PCT/IN2014/000687, International Preliminary Report on Patentability mailed May 12, 2016", 6 pgs.
Bhuniya, Rajib, et al., "Asymmetric synthesis of both the enantiomers of antidepressant venlafaxine and its analogues", *Tetrahedron Letters*, 53(15), (2012), 1990-1992.
Chavan, Subhash P., et al., "An efficient and green protocol for the preparation of cycloalkanols: a practical synthesis of venlafaxine", *Tetrahedron Letters*, 45, (2004), 7291-7295.
Kavitha, C. V., et al., "Synthesis of new bioactive venlafaxine analogs: Novel thiazolidin-4-ones as antimocrobials", *Bioorganic & Medicinal Chemistry*, 14, (2006), 2290-2299.
"International Application No. PCT/IN2014/000687, International Search Report and Written Opinion mailed Mar. 10, 2015", (Mar. 10, 2015), 7 pgs.
Chavan, Subhash P., et al., "Asymmetric total synthesis of (−)-venlafaxine using an organocatalyst", Tetrahedron Letters, vol. 54, Issue 17, Apr. 24, 2013, pp. 2137-2139, (Apr. 24, 2013), 2137-2139.

* cited by examiner

*Primary Examiner* — Clinton Brooks
(74) *Attorney, Agent, or Firm* — Schwegman Lundberg & Woessner, P.A.

(57) ABSTRACT

There is a need for short, resolution free asymmetric process for synthesis of one isomer of venlafaxine, (−)-venlafaxine. The invention provides a novel, short process of synthesis of (−)-venlafaxine, with yield greater than 50% and ee>99%. This process can be used for racemic synthesis of venlafaxine with overall yield 65%.

10 Claims, 2 Drawing Sheets

PROCESS FOR TOTAL SYNTHESIS OF VENLAFAXINE

PRIORITY CLAIM TO RELATED APPLICATIONS

This application is a U.S. national stage application filed under 35 U.S.C. §371 from International Application Serial No. PCT/IN2014/000687, which was filed 29 Oct. 2014, and published as WO2015/063791 on 7 May 2015, and which claims priority to India Application No. 3197/DEL/2013, filed 29 Oct. 2013, which applications and publication are incorporated by reference as if reproduced herein and made a part hereof in their entirety, and the benefit of priority of each of which is claimed herein.

FIELD OF THE INVENTION

The present invention relates to a novel process for the total synthesis of venlafaxine and its enantiomer. The present invention particularly relates to a process for the synthesis of venlafaxine using Sharpless asymmetric epoxidation followed by epoxide opening. More particularly, the invention relates to a process for the selective synthesis of one enantiomer of venlafaxine via a protecting group free approach.

BACKGROUND OF THE INVENTION

Development of a number of nontricyclic antidepressants with reduced or completely diminished cardiovascular or anticholinergic liability has been reported in recent years. Among those one of the most prescribed antidepressants is venlafaxine, which is a unique drug with well documented efficacy & safety in the acute treatment of major depressive disorder. It was first time released for clinical trials in 1994 by Wyeth Company, now part of Pfizer and globally marketed as effexor R®. It has now become widely recognised as an effective first line agent in the treatment of major depressive disorder (MDD), generalized anxiety disorder, and comorbid indications in certain anxiety disorder for depression. It was a top selling drug from 2006, to 2008 and sixth most prescribed antidepressant in US in the year 2007. In 2010, it ranked $25^{th}$ in top 200 brand name drugs by total US prescriptions.

Venlafaxine is marketed in racemic form, although both R & S enantiomers show different bio activities i.e. S-enantiomer is a selective serotonin reuptake inhibitor, while R enantiomer is more selective towards norepinephrine transporter. Also, it has either no or has little activity on a variety of neuroreceptors.

Article titled, "An efficient and green protocol for the preparation of cycloalkanols: a practical synthesis of venlafaxine" by Subhash P. Chavan in Tetrahedron Letters, Volume 45. Issue 39, 20 Sep. 2004, Pages 7291-7295 reports The condensation of arylacetonitriles with cyclic ketones using aqueous NaOH or KOH under phase transfer catalysis to give almost quantitative yields of cycloalkanols. This protocol is utilized for a practical synthesis of the antidepression drug, venlafaxine 1.

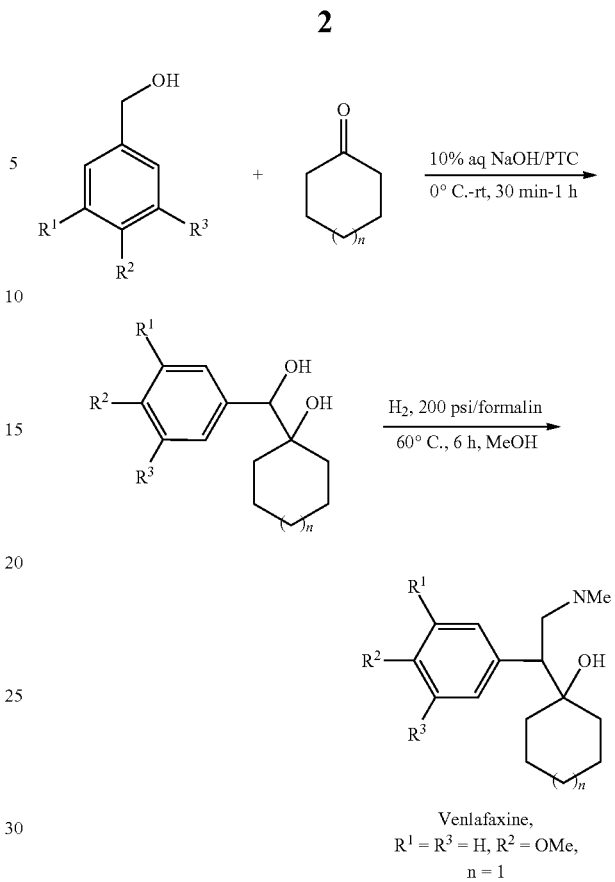

Venlafaxine,
$R^1 = R^3 = H$, $R^2 = OMe$,
$n = 1$

Article titled, "Asymmetric synthesis of both the enantiomers of antidepressant venlafaxine and its analogues" by Rajib Bhuniya, Samik Nanda in Tetrahedron Letters, Volume 53, Issue 15, 11 Apr. 2012, Pages 1990-1992 reports Chemoenzymatic asymmetric synthesis of antidepressant agent venlafaxine and its analogue. The main highlight of the reported synthesis is the stereoselective synthesis of cyanohydrins by (S)-hydroxynitrile lyase (*Hevea brasiliensis*) followed by lipase catalyzed kinetic resolution.

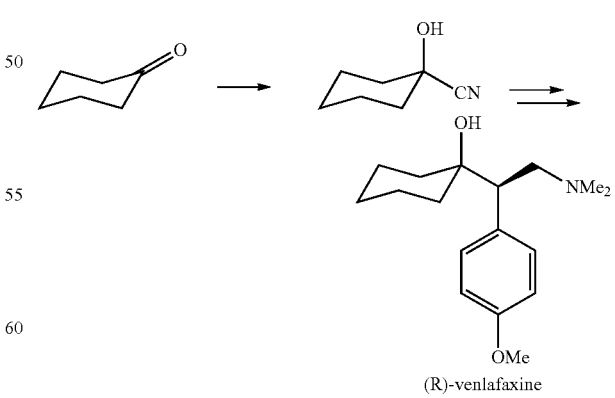

(R)-venlafaxine

U.S. Pat. No. 6,756,502 B2 discloses a process for the preparation of Venlafaxine via the novel epoxy-nitrile intermediate,

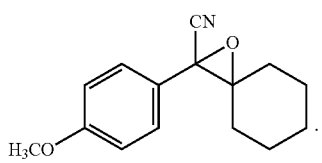
(I)

Article titled, "Asymmetric total synthesis of (−)-venlafaxine using an organocatalyst" by Subhash P. Chavan in Tetrahedron Letters, Volume 54, Issue 17, 24 Apr. 2013, Pages 2137-2139 reports that an asymmetric total synthesis of (−)-venlafaxine using an organocatalyst has been achieved via a unified strategy employing organocatalytic Michael addition, regio-selective dehydration and selective epoxide ring opening.

US 2007/0135449 A1 discloses a process for selectively synthesising the desired enantiomer of an intermediate useful in the production of a 2-phenyl-2-(1-hydroxycycloalkyl) ethylamines of formula 1:

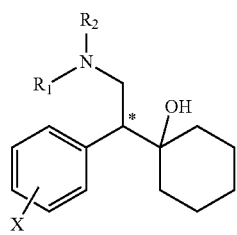
I wherein X is $OCH_3$ or $CF_3$, $R_1$ and $R_2$ are each independently selected from $C_1$-$C_3$ alkyl, or together with the nitrogen they are attached from a 1,4-piperazine ring wherein said piperazine ring is substituted with from 0 to 2 methyl groups. The process of the invention comprises the steps of: treating a (4S or 4R)-4-benzyl-3-[(methoxyphenyl) acetyl]-1,3-oxazolidin-2-one having the structure

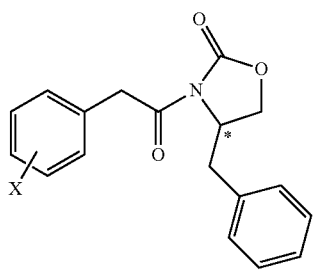

wherein X is selected from the group consisting of methoxy or trifluoromethoxy; with a base under conditions which permit formation of the corresponding anion; and mixing the corresponding anion with cyclohexanone under conditions which permit an aldol reaction to form the corresponding (4S or 4R)-4-benzyl-3-[(2R or 2S)-2-(1-hydroxycyclohexyl)-(methoxyphenyl)acetyl]-1,3-oxazolidin-2-one.

Article titled, "Simple and an efficient method for the synthesis of 1-[2-dimethylamino-1-(4-methoxy-phenyl)-ethyl]-cyclohexanol hydrochloride: (±) venlafaxine racemic mixtures" by Basappa, C. V. Kavitha, K. S. Rangappa in Bioorganic & Medicinal Chemistry Letters, Volume 14, Issue 12, 21 Jun. 2004, Pages 3279-3281 reports a novel synthetic method was developed for the synthesis of venlafaxine using inexpensive reagents.

WO 2010046808 A2 discloses a process for the preparation of Venlafaxine Hydrochloride comprising steps of i) treating 4-methoxyphenyl acetonitrile with cyclohexanone in presence of alkali hydroxide and super base to get 1-[cyano (4-methoxyphenyl) methyl] cyclohexanol and ii) reducing 1-[cyano (4-methoxyphenyl) methyl] cyclohexanol in presence of catalyst, activator and alcoholic ammonia under hydrogen pressure.

Therefore it is the need to develop an efficient process for asymmetric synthesis of venlafaxine, wherein one enantiomer is obtained in high enantiomeric purity.

OBJECTIVE OF THE INVENTION

One object of the invention is to provide a short process for asymmetric synthesis of venlafaxine, wherein one enantiomer is obtained in high enantiomeric purity.

Another object of the invention is to provide a process to those results selectively in one enantiomer of venlafaxine, without the need for a step of resolution and with improved yields.

SUMMARY OF THE INVENTION

In accordance with the object above the present invention provides a short process for asymmetric synthesis of venlafaxine, wherein one enantiomer is obtained in high enantiomeric purity.

In accordance with the object above the present invention further provides a process for selective synthesis of one enantiomer of venlafaxine, via a protecting group free approach, without the need for a step of resolution and with improved yields.

Accordingly the present invention provides a process for the synthesis of venlafaxine of formula 1 or its enantiomer, Formula 1

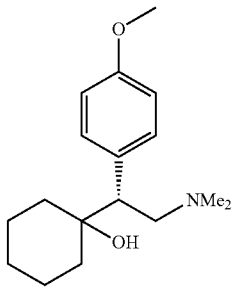

wherein the process comprising the steps:
a. homologating carbonyl of cyclohexanone with two carbon Wittig ylide with heating at 50° C. to 140° C. in toluene to obtain α, β-unsaturated ester;
b. subjecting the ester of step (a) to selective ester reduction by Red-Al to give allyl alcohol;
c. subjecting allyl alcohol of step (b) for epoxidation reaction to afford epoxide;
d. treating the epoxide of step (c) with methane sulphonyl chloride and triethyl amine to obtain crude mesylate, which on subsequently subjecting for amination in 40% aqueous dimethyl amine solution at room temperature to afford the epoxy amine; and e. treating epoxy amine of step (d) with p-methoxyphenyl magnesium bromide in presence of catalytic copper iodide to furnish venlafaxine.

In an embodiment of the invention wherein the epoxidation in step (c) is carried out by the method selected from a group consisting of Sharpless epoxidation or by mCPBA in presence of NaHCO$_3$ to produce chiral or racemic epoxide respectively.

In a further embodiment of the invention in, step (a), wherein the temperature is ranging between 50-140° C. and reflux time is ranging between 20-24 h.

In another embodiment of the invention wherein, step (b), wherein the temperature is 0° C. and stirring time is 10 to 30 mins.

In yet another embodiment of the invention wherein, step (c), wherein the temperature is in the range of 20 to 35° C. and stirring time is 6-8 h.

In one more embodiment of the invention wherein, step (d), wherein the epoxidation is carried out at temperature in the range of 0° C. to 60° C. and stirring time is ranging between 10-12 h.

In still another embodiment of the invention wherein Sharpless asymmetric epoxidation for synthesis of asymmetric venlafaxine is carried out at a temperature ranging between −20 to −50° C. to obtain chiral epoxide.

In one more embodiment of the invention wherein, step (e), wherein the temperature is −30-to-40° C. and stirring for a period ranging between 4-5 h.

In a further embodiment of the invention wherein, the yield is preferably 53% with ee>99%.

In an embodiment of the invention wherein, the yield is preferably >64% for racemic venlafaxine ((±)-venlafaxine).

LIST OF ABBREVIATIONS USED tBuOOH: tert-butyl hydrogen peroxide
DET: Diethyl tartarate
THF: Tetrahydrofuran.
Ms: Methanesulphonyl
m-CPBA: meta-Chloroperoxybenzoic acid.
DCM: Dichloromethane

DETAILED DESCRIPTION OF THE INVENTION

Figure 1:
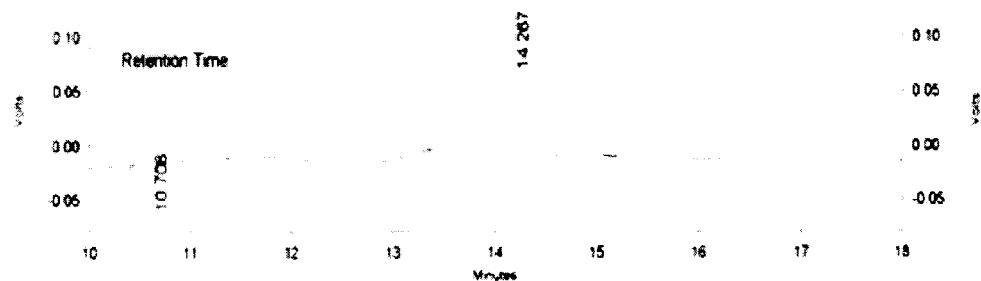
FIG. 1: Chromatogram for racemic venlafaxine
Figure 2:
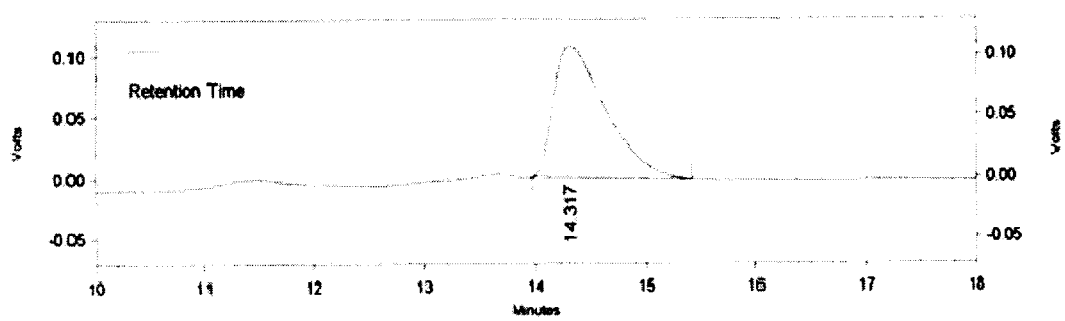
FIG. 2: Chromatogram for optically pure venlafaxine

In view of above the present invention provides a process for the synthesis of venlafaxine via a protecting group free approach.

In an embodiment the present invention provides a process for the synthesis of (−)-venlafaxine compound of formula 1,

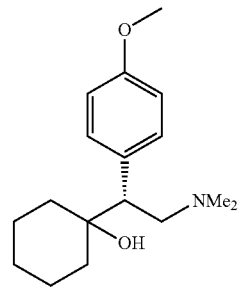

Formula 1 comprising the steps:
a. homologating carbonyl of cyclohexanone 6 with two carbon Wittig ylide with refluxing in toluene to obtain α, β-unsaturated ester 5 in >95% yield;
b. subjecting the ester 5 of step (a) to selective ester reduction by Red-Al to give allyl alcohol 4 in >95% yield;
c. subjecting allyl alcohol 4 of step (b) for Sharpless epoxidation reaction to afford >80% yield of chiral epoxide 3 and >82% enantiomeric excess (ee);
d. treating epoxide 3 of step (c) with methane sulphonyl chloride and triethyl amine to obtain crude mesylate, which on subsequently subjecting for amination in 40% aqueous dimethyl amine solution at room temperature afforded the chiral epoxy amine 2 in >90% yield; and
e. treating chiral epoxy amine of step (d) with p-methoxyphenyl magnesium bromide in presence of catalytic copper iodide to afford (−)-venlafaxine 1 in >50% yield with ≥99% ee after recrystalisation.

In a preferred embodiment the present invention provides a process for the synthesis of (−)-venlafaxine of formula 1 with yield >50% and ee>99%.

The above process is shown below in Scheme 1:

Scheme: 1 Total synthesis of asymmetric (-)-venlafaxine.

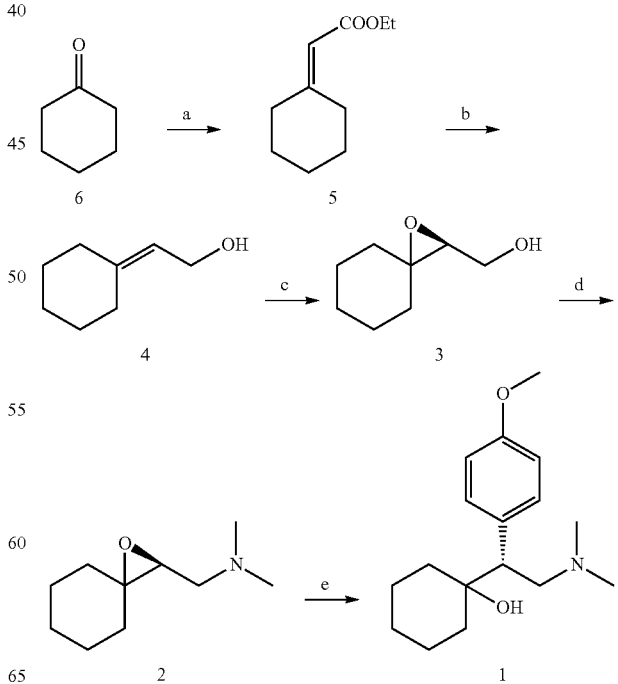

In another embodiment the present invention provides a process for the synthesis of racemic venlafaxine 9 comprising the steps:

a. homologating carbonyl of cyclohexanone 6 with two carbon Wittig ylide with refluxing in toluene to obtain α, β-unsaturated ester 5 in >95% yield;
b. subjecting the ester 5 of step (a) to selective ester reduction by Red-Al (commercially known as Vittride) to give allyl alcohol 4 in >95% yield;
c. treating allyl alcohol 4 of step (b) with NaHCO$_3$ and mCPBA respectively followed by work-up to afford the epoxy alcohol 7;
d. treating epoxy alcohol 7 of step (c) with methane sulphonyl chloride and triethyl amine to obtain crude mesylate, which on subsequently subjecting for amination in 40% aqueous dimethyl amine solution at room temperature afforded the epoxy amine 8; and
e. treating epoxy amine 8 of step (d) with p-methoxyphenyl magnesium bromide in presence of catalytic copper iodide to afford racemic venlafaxine 9.

In a preferred embodiment the present invention provides a process for the synthesis of racemic venlafaxine 9 with yield >70%.

The above process is shown below in Scheme 2:

Scheme: 2 Total synthesis of (±)-venlafaxine.

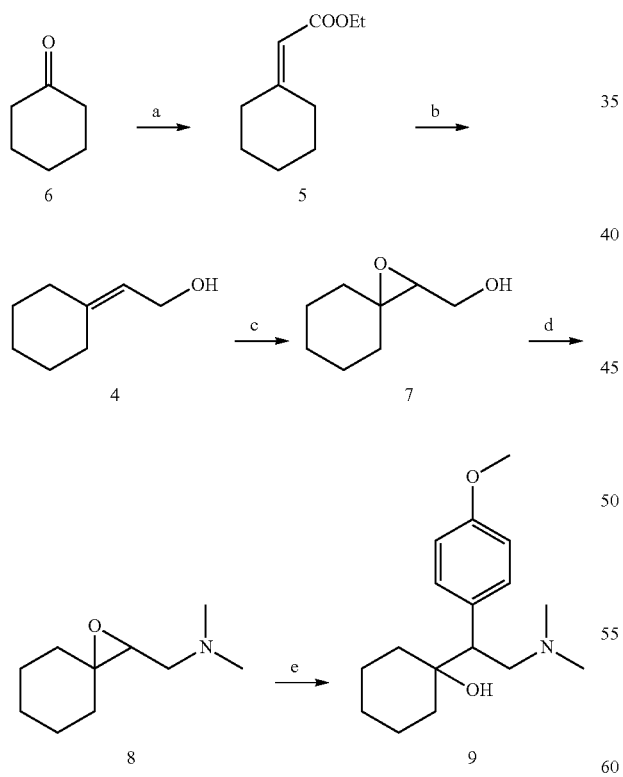

The invention will now be described in detail in connection with certain preferred and optional embodiments, so that various aspects thereof may be more fully understood and appreciated.

EXAMPLES

Example 1

Ethyl 2-cyclohexylideneacetate (5)

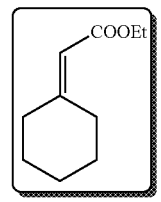

A clean, dry 250 mL R.B. was charged with cyclohexanone (5 g, 51.00 mmol) and two carbon Wittig ylide (19.537 gm, 56.1 mmol). Then, temperature was raised to 120° C. The reaction mixture was refluxed for 24 h. After completion of the reaction, toluene was removed in vacuo.

After removal of toluene, it was filtered in 5% ethyl acetate:pet. ether system through 3 cm thick celite bed to remove triphenyl phosphorous oxide. Filtrate was concentrated under reduced pressure and purification of the residue on a silica gel column chromatography using ethyl acetate/pet. ether (2:98) gave unsaturated ester 4 (24.7 g, 98%) as a clear liquid. R$_f$ (5% EtOAc/hexane): 0.5.

Yield: 98%; IR (CHCl$_3$): 3020, 1705, 1646, 1215 cm$^{-1}$; $^1$H NMR (200 MHz, Chloroform-d+CCl$_4$) δ ppm 1.28 (t, J=7.1 Hz, 3H) 1.50-1.76 (m, 7H) 2.10-2.27 (m, 2H) 2.64-3.01 (m, 2H) 4.13 (q, J=7.1 Hz, 2H) 5.58 (t, J=1.0 Hz, 1H); $^{13}$C NMR (50 MHz, CHLOROFORM-d+CCl$_4$) δ ppm 14.15, 26.14, 27.61, 28.46, 29.55, 37.80, 59.05, 112.96, 162.89, 166.28.

Example 2

2-Cyclohexylideneethan-1-ol (4)

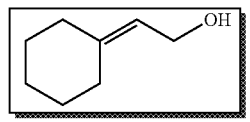

To a solution of vitride in toluene at 0° C. (1.5 eq), unsaturated ester 5 in toluene was added in drop wise manner, and the solution was stirred at same temperature for 30 min. The reaction was then quenched with saturated sodium potassium tartarate salt and stirred for 3 h. The solution was extracted with ethyl acetate (3×100 mL), washed with water followed by brine, dried over anhydrous Na$_2$SO$_4$ and filtered. Removal of the ethyl acetate under reduced pressure furnished compound 4 as a clear liquid and was characterized without any purification method (6.1 g, 97%). R$_f$ (40% EtOAc/hexane): 0.4.

Yield: 97%; IR (CHCl$_3$): 3421, 2934, 1647, 1705, 1265 cm$^{-1}$; $^1$H NMR (200 MHz. Chloroform-d+CCl$_4$) δ ppm 1.48-1.69 (m, 6H) 2.01-2.29 (m, 4H) 3.50 (s, 1H) 4.13 (d, J=7.1 Hz, 2H) 5.36 (tt, J=7.1 Hz, 1H); $^{13}$C NMR (50 MHz, chloroform-d+CCl$_4$) δ ppm 26.66, 27.76, 28.32, 28.77, 36.98, 58.21, 120.47, 143.76.

Example 3

(S)-(1-Oxaspiro[2.5]octan-2-yl)methanol (3)

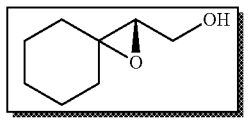

To a stirred solution of Ti(O-iPr)$_4$ (7.88 g, 55.5 mmol) an molecular sieves 4 A° in dry DCM (40 mL) was added L(+)-diethyl tartarate (11.46 g, 55.5 mmol) at −10° C. After stirring for 10 min, TBHP (4M in toluene, 10 g, 111.08 mmol) was added drop wise to the reaction mixture. After 30 minutes, temperature of the reaction mixture was lowered to −50° C. A solution of allyl alcohol 4 (3.5 g, 27.77 mmol) in DCM was added drop wise to the reaction mixture under nitrogen atmosphere. Reaction mixture was stirred for 6 h. The progress of reaction was monitored by TLC. After completion of reaction, reaction was quenched by adding aqueous NaOH solution and stirring for 2 hours at room temperature. Then organic and aqueous layers were separated. Aqueous layer was extracted with DCM (3×50 mL). The combined organic layers were dried over anhydrous Na$_2$SO$_4$, filtered and concentrated to dryness under reduced pressure. Purification of the residue on a silica gel column using ethyl acetate:pet. ether (30:70) as eluent furnished the epoxy alcohol 3 (83%) as a colorless liquid. R$_f$ (40%, EtOAc:PE): 0.3.

[α]$_D^{25}$=−17.02 (c=1.03, CHCl$_3$); Lit. [α]$_D^{25}$=−16.1 (c=1.0, CHCl$_3$); Yield: 83%; IR (CHCl$_3$): 3421, 2934, 1647, 1705, 1265 cm$^{-1}$; $^1$H NMR (200 MHz, Chloroform-d+CCl$_4$) δ 1.44-1.90 (m, 11H), 2.94 (dd, J=6.63, 4.48 Hz, 1H), 3.53-3.98 (m, 2H) $^{13}$C NMR (50 MHz, Cchloroform-d+CCl$_4$) δ 24.68, 25.45, 29.31, 35.22, 60.52, 63.29, 64.31.

HRMS: 165.0887 [M+Na]$^+$. Exact mass: 142.0994

Example 4

(S)—N,N-dimethyl-1-(1-oxaspiro[2.5]octan-2-yl)methanamine (2)

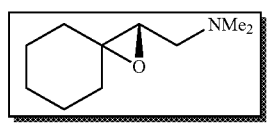

To a solution of ethyl epoxy alcohol 3 (2.5 gm, 17.6 mmol) in anhydrous CH$_2$Cl$_2$ (5 mL) was added Et$_3$N (5.33 gm, 7.32 ml, 52.81 mmol) at 0° C. and Methane sulphonyl chloride (3.0 gm, 2.15 ml, 26.4 mmol) sequentially in drop wise manner. Progress of the reaction was monitored by TLC. After completion, the reaction was quenched with water (5 mL) and the organic layer was washed with aq NaHCO$_3$ (2%, 10 mL). The organic layer was dried over anhydrous Na$_2$SO$_4$, filtered and concentrated under vacuum. The crude compound was used directly in the next reaction. To crude mesylate epoxide (4 gm, 18.18 mmol) was added 40% aqueous solution of N,N-dimethyl amine (72.72 mmol) and stirred at room temperature for 10 h. The reaction mixture was directly concentrated under reduced pressure at 60° C. to furnish crude residue of epoxy amine. The crude residue was purified by silica gel column chromatography to get 95% of epoxy amine 2 as yellow oil.

[α]$_D^{25}$=−18.41 (c=1.4, CHCl$_3$); Yield: 95%; $^1$H NMR (200 MHz, Chloroform-d+CCl$_4$) δ 1.40-1.80 (m, 10H), 2.20-2.39 (m, 7H), 2.56-2.73 (m, 1H), 2.84 (dd, J=6.25, 3.98 Hz, 1H); $^{13}$C NMR (50 MHz, Chloroform-d+CCl$_4$) δ ppm 24.42, 24.49, 25.42, 29.26, 35.11, 45.54, 57.70, 61.06, 62.43, HRMS: 170.1539[M+H]$^+$. Exact mass: 169.1467

Example 5

Synthesis of (−)-Venlafaxine (1)

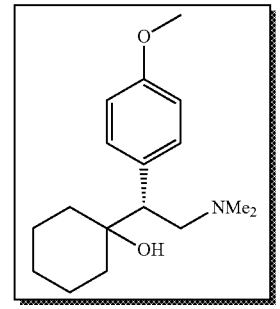

4-Bromoanisole (1.66 gm, 8.86 mmol) was added to the suspension of Mg metal turnings (425 mg, 17.7 mmol) in dry THF and the resulting mixture was allowed to stir under heating until all magnesium metal disappears. To this solution was added a mixture of copper iodide (112 mg, 0.59 mmol) and allowed to stir for 15 min. This suspension was cooled to −40° C. A solution of (−)-epoxy amine 2 (1 g, 5.9 mmol) in THF (40 mL) was added slowly to the above reagent and the mixture was stirred at −40° C. for 4 h. The reaction mixture was quenched with a saturated solution of NH$_4$Cl. The organic layer and aqueous layers were separated. Aqueous layer was extracted with EtOAc (3×50 mL). The combined organic layers were washed with brine, dried over anhydrous Na$_2$SO$_4$, filtered and concentrated to dryness under reduced pressure. Purification of the residue on a silica gel column using ethyl acetate as eluent furnished the (−)-venlafaxine 1 (89% over two steps) as white solid.

Characterization Data of (−)-Venlafaxine:

The product of the process enlisted in example 1 was characterized by IR and $^1$H and $^{13}$C NMR and results are as follows:

R$_f$(100% EtOAc) 0.2 (long tail); IR (CHCl$_3$): 3164, 2982, 2938, 2860, 2782, 1610, 1512 cm$^{-1}$;

[α]$_D^{25}$: −24.285 (c=1.04, EtOH) Literature R-(−)-venlafaxine [α]$_D^{25}$=−29.9 (c=1.04, EtOH).

IR (CHCl$_3$): 3164, 2982, 2938, 2860, 2782, 1610 cm$^{-1}$; $^1$H NMR (400 MHz, Chloroform-d+CCl$_4$) δ ppm 0.73-1.11 (m, 2H) 1.33-1.74 (m, 8H) 2.35-2.51 (m, 7H) 3.01 (d, 1H) 3.00 (dd, J=11.9, 2.9 Hz, 1H) 3.41 (t, J=11.9 Hz, 1H) 3.79 (s, 3H) 5.49 (s, 1H) 6.79 (d, J=8.8 Hz, 2H) 7.04 (d, 2H); $^{13}$C NMR (101 MHz, Chloroform-d+CCl$_4$) δ ppm 21.36, 21.54, 25.90, 31.29, 37.84, 45.35, 51.74, 55.06, 61.15, 74.22, 76.68, 77.31, 113.49, 130.08, 132.32, 158.44; HRMS: 278.2115 [M+H]$^+$. Exact mass: 277.2042

Optical Purity of (−)-Venlafaxine (R)-venlafaxine [α]$_D^{25}$=−24.285 (c=1.04, EtOH).

Column: Kromasil 5-Amy Coat (250×4.6 mm)

Mobile Phase: EtOH:Pet ether:Diethylamine (05:95:0.5)
Wave length: 254 nm

| Retention time | Area % |
| --- | --- |
| 10.708 | 50.501 |
| 14.267 | 49.499 |

| Retention time | Area % |
| --- | --- |
| 14.317 | 100.000 |

Example: 6

1-Oxaspiro[2.5]octan-2-ylmethanol (7)

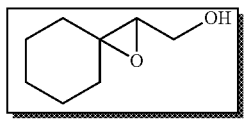

To a stirred solution of allyl alcohol (4.6 gm, 36.51 mmol) in DCM was added NaHCO$_3$ (6.1 gm, 73.01 mmols) and mCPBA (8.256 gm, 47.46 mmols) respectively at 0° C. and the reaction mixture was stirred for 3 h. The progress of reaction was monitored by TLC. After completion of reaction, reaction mixture was quenched by adding saturated aq NaHCO$_3$ solution and stirring for 2 hours at room temperature. The organic and aqueous layers were separated. Aqueous layer was extracted with DCM (3×50 mL). The combined organic layers were dried over anhydrous Na$_2$SO$_4$, filtered and concentrated to dryness under reduced pressure. Purification of the residue on a silica gel column using ethyl acetate:pet ether (30:70) as eluent furnished the epoxy alcohol (94%) as a colorless liquid. R$_f$ (40%, EtOAc:PE): 0.4.

Yield: 94%; IR (CHCl$_3$): 3421, 2934, 1647, 1705, 1265 cm$^{-1}$; $^1$H NMR (200 MHz, Chloroform-d+CCl$_4$) δ 1.44-1.90 (m, 11H), 2.94 (dd, J=6.63, 4.48 Hz, 1H), 3.53-3.98 (m, 2H); $^{13}$C NMR (50 MHz, Chloroform-d+CCl$_4$) δ 24.68, 25.45, 29.31, 35.22, 60.52, 63.29, 64.31; HRMS: 165.0887 [M+Na]$^+$.

N,N-Dimethyl-1-(1-oxaspiro[2.5]octan-2-yl)methanamine (8)

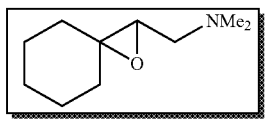

To a solution of ethyl epoxy alcohol 7 (2.5 gm, 17.6 mmol) in anhydrous CH$_2$Cl$_2$ (5 mL) was added Et$_3$N (5.33 gm, 7.32 ml, 52.81 mmol) at 0° C. and Methane sulphonyl chloride (3.0 gm, 2.15 ml, 26.4 mmol) sequentially in drop wise manner. Progress of the reaction was monitored by TLC. After completion, the reaction was quenched with water (5 mL) and the organic layer was washed with aq NaHCO$_3$ (2%, 10 mL). The organic layer was dried over anhydrous Na$_2$SO$_4$, filtered and concentrated under vacuum. The crude compound was used directly in the next reaction. To crude mesylate epoxide (4 gm, 18.18 mmol) was added 40% aqueous solution of N,N-dimethyl amine (72.72 mmol) and stirred at room temperature for 10 h. The reaction mixture was directly concentrated under reduced pressure at 60° C. to furnish crude residue of epoxy amine. The crude residue was purified by silica gel column chromatography to get 95% of epoxy amine 8 as yellow oil.

Yield: 95%; $^1$H NMR (200 MHz, Chloroform-d+CCl$_4$) δ 1.40-1.80 (m, 10H), 2.20-2.39 (m, 7H), 2.56-2.73 (m, 1H), 2.84 (dd, J=6.25, 3.98 Hz, 1H); $^{13}$C NMR (50 MHz, Chloroform-d+CCl$_4$) δ ppm 24.42, 24.49, 25.42, 29.26, 35.11, 45.54, 57.70, 61.06, 62.43, HRMS: 170.1539 [M+H]$^+$. Exact mass: 169.1467

Example 5

Synthesis of (±)-Venlafaxine (9)

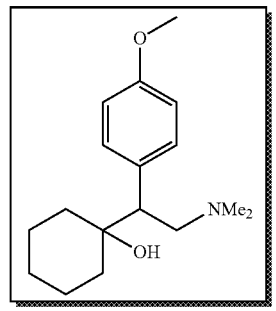

4-Bromoanisole (1.66 gm, 8.86 mmol) was added to the suspension of Mg metal turnings (425 mg, 17.7 mmol) in dry THF and the resulting mixture was allowed to stir under heating until all magnesium metal disappears. To this solution was added a mixture of copper iodide (112 mg, 0.59 mmol) and allowed to stir for 15 min. This suspension was cooled to −40° C. A solution of (−)-epoxy amine 8 (1 g, 5.9 mmol) in THF (40 mL) was added slowly to the above reagent and the mixture was stirred at −40° C. for 4 h. The reaction mixture was quenched with a saturated solution of NH$_4$Cl. The organic layer and aqueous layers were separated. Aqueous layer was extracted with EtOAc (3×50 mL). The combined organic layers were washed with brine, dried over anhydrous Na$_2$SO$_4$, filtered and concentrated to dryness under reduced pressure. Purification of the residue on a silica gel column using ethyl acetate as eluent furnished the (±)-venlafaxine 9 (89% over two steps) as white solid.

Synthesis of (±)-Venlafaxine (9)

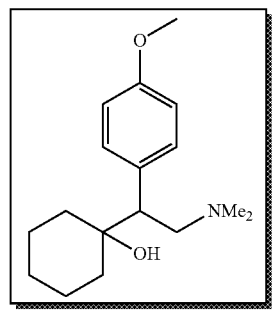

The product of the process enlisted in example 9 was characterized by IR and $^1$H and $^{13}$C NMR and results are as follows:

R$_f$ (100% EtOAc) 0.2 (long tail); IR (CHCl$_3$): 3164, 2982, 2938, 2860, 2782, 1610, 1512 cm$^{-1}$; IR (CHCl$_3$): 3164, 2982, 2938, 2860, 2782, 1610 cm$^{-1}$; $^1$H NMR (400 MHz, Chloroform-d+CCl$_4$) δ ppm 0.73-1.11 (m, 2H) 1.33-1.74 (m, 8H) 2.35-2.51 (m, 7H) 3.01 (d, 1H) 3.00 (dd, J=11.9, 2.9 Hz, 1H) 3.41 (t, J=11.9 Hz, 1H) 3.79 (s, 3H) 5.49 (s, 1H) 6.79 (d, J=8.8 Hz, 2H) 7.04 (d, 2H); $^{13}$C NMR (101 MHz, Chloroform-d+CCl$_4$) δ ppm 21.36, 21.54, 25.90, 31.29, 37.84, 45.35, 51.74, 55.06, 61.15, 74.22, 76.68, 77.31, 113.49, 130.08, 132.32, 158.44; HRMS: 278.2115 [M+H]$^+$. Exact mass: 277.2042

Advantages of Invention:
1. Use of cheap and easily available raw materials with environmentally friendly reaction conditions makes the process highly useful for industry
2. Expensive catalyst free and resolution step free process with improved overall yields with Enantiomeric purity >99%.
3. The process can decrease the cost of venlafaxine production which will reduce the price of anti-depressents.

We claim:

1. A process for the synthesis of venlafaxine of formula 1 or its enantiomer,

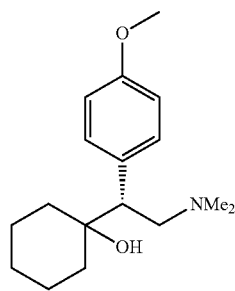

Formula 1 wherein the process comprising the steps:
a. homologating carbonyl of cyclohexanone with two carbon Wittig ylide with heating at 50° C. to 140° C. in toluene to obtain α, β-unsaturated ester;
b. subjecting the ester of step (a) to selective ester reduction by Red-Al to give allyl alcohol;
c. subjecting allyl alcohol of step (b) for epoxidation reaction to afford epoxide;
d. treating the epoxide of step (c) with methane sulphonyl chloride and triethyl amine to obtain crude mesylate, which on subsequently subjecting for amination in 40% aqueous dimethyl amine solution at room temperature to affords the epoxy amine; and
e. treating epoxy amine of step (d) with p-methoxyphenyl magnesium bromide in presence of catalytic copper iodide to furnish venlafaxine.

2. The process according to claim 1 wherein the epoxidation in step (c) is carried out by the method selected from a group consisting of Sharpless epoxidation or by mCPBA in presence of NaHCO$_3$ to produce chiral or racemic epoxide respectively.

3. The process according to claim 1, step (a), wherein the temperature is ranging between 50-140° C. and reflux time is ranging between 20-24 h.

4. The process according to claim 1, step (b), wherein the temperature is 0° C. and stirring time is 10 to 30 mins.

5. The process according to claim 1, step (c), wherein the temperature is in the range of 20 to 35° C. and stirring time is 6-8 h.

6. The process according to claim 1, step (d), wherein the epoxidation is carried out at temperature in the range of 0° C. to 60° C. and stirring time is ranging between 10-12 h.

7. The process according to claim 1 wherein Sharpless asymmetric epoxidation for synthesis of asymmetric venlafaxine is carried out at a temperature ranging between −20 to −50° C. to obtain chiral epoxide.

8. The process according to claim 1, step (e), wherein the temperature is −30-to-40° C. and stirring for a period ranging between 4-5 h.

9. The process according to claim 1, wherein the yield is preferably 53% with ee>99%.

10. The process according to claim 1, wherein the yield is preferably >64% for racemic venlafaxine ((±)-venlafaxine).

* * * * *